United States Patent [19]

Kikumoto et al.

[11] Patent Number: 4,485,258

[45] Date of Patent: Nov. 27, 1984

[54] PHARMACEUTICALLY ACTIVE (3-AMINOPROPOXY)BIBENZYL DERIVATIVES

[75] Inventors: Ryoji Kikumoto, Machida; Harukazu Fukami, Yokohama; Hiroto Hara; Kunihiro Ninomiya, both of Machida; Mamoru Sugano, Tokyo, all of Japan

[73] Assignee: Mitsubishi Chemical Industries Limited, Tokyo, Japan

[21] Appl. No.: 403,119

[22] Filed: Jul. 29, 1982

[30] Foreign Application Priority Data

Aug. 20, 1981 [JP] Japan ................................ 56-130704

[51] Int. Cl.$^3$ ........................................... C07C 59/68
[52] U.S. Cl. ..................................... 562/471; 562/444; 560/123; 560/127; 560/193; 564/347; 564/348; 544/386; 544/391; 546/192; 546/225; 548/570; 548/578; 421/317; 421/330; 421/250; 421/274; 421/340

[58] Field of Search ................ 564/347, 348; 562/444, 562/451, 471; 560/193, 123, 127

[56] References Cited

U.S. PATENT DOCUMENTS 3,930,016 12/1975 Berntsson et al. ................... 564/348
4,071,552 1/1978 Ferland et al. ...................... 562/444

FOREIGN PATENT DOCUMENTS 3065836 6/1978 Japan ................................... 564/384
31136 8/1980 Japan ................................... 564/384
6123954 1/1981 Japan ................................... 564/384
6029549 3/1981 Japan ................................... 564/348
6029550 3/1981 Japan ................................... 564/384

*Primary Examiner*—Paul J. Killos
*Attorney, Agent, or Firm*—Oblon, Fisher, Spivak, McClelland & Maier

[57] ABSTRACT

(3-Aminopropoxy)bibenzyl derivatives are prepared and found useful as pharmaceutical agents, particularly as inhibitors of platelet aggregation.

13 Claims, No Drawings

PHARMACEUTICALLY ACTIVE (3-AMINOPROPOXY)BIBENZYL DERIVATIVES

BACKGROUND OF THE INVENTION

1. Field of the Invention

This invention relates to (3-aminopropoxy)bibenzyl derivatives which possess anticoagulant activity, especially activity against blood platelet aggregation. They enhance the prostaglandins $I_2$ activity and are effective for the cure and prevention of thrombosis.

More particularly, this invention relates to (3-aminopropoxy)bibenzyl derivatives and to pharmaceutical compositions containing the same effective for inhibiting platelet aggregation.

This invention also relates to processes whereby said (3-aminopropoxy)bibenzyl derivatives are prepared and also to processes for inhibiting platelet aggregation.

SUMMARY OF THE INVENTION

In summary, the compounds of this invention can be represented by the formula (I):

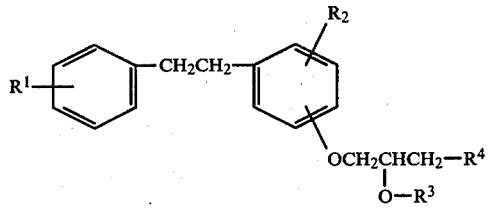

wherein $R^1$ and $R^2$ independently are hydrogen, halogen, $C_1-C_5$ alkyl, $C_1-C_5$ alkoxy or $C_2-C_6$ dialkylamino; $R^3$ is hydrogen, $-(CH_2)_n-COOH$ where n is an integer of 1 to 5, or

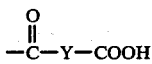

where Y is $-(CH_2)_m-$ (m is an integer of 1 to 3),

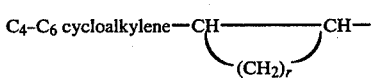

where r is an integer of 2 to 4, or

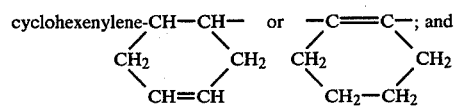

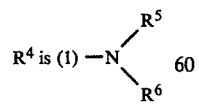

wherein $R^5$ and $R^6$ independently are $C_1-C_8$ alkyl or (2)

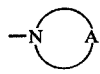

wherein A is a divalent radical which consists of two or more groups selected from methylene $-CH_2-$ and monosubstituted

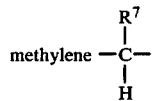

where $R^7$ is $C_1-C_5$ alkyl or carbamoyl $-CONH_2$ and zero or one or more than one group selected from the group consisting of

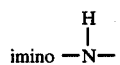

and substituted

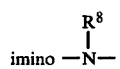

where $R^8$ is $C_1-C_5$ alkyl, which are combined in an arbitory order to form a ring, the number of the combined groups being up to 9, or a pharmaceutically acceptable acid addition salt thereof.

DESCRIPTION OF THE PREFERRED EMBODIMENTS

As summarized above, this invention relates to a group of compounds useful as pharmaceutical agents, the structure and numbering system of which are as follows:

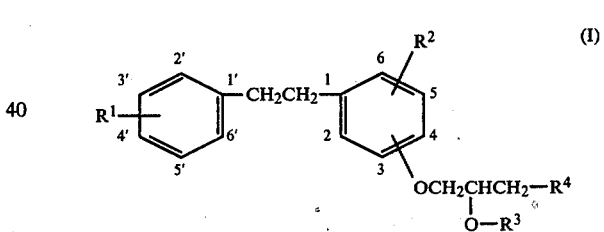

In the above formula (I), $R^1$ and $R^2$ independently are hydrogen; halogen such as fluorine, chlorine and bromine (preferably fluorine and chlorine); $C_1-C_5$ (preferably $C_1-C_3$) alkyl such as methyl, ethyl, propyl, butyl or the like; $C_1-C_5$ (preferably $C_1-C_3$) alkoxy such as methoxy, ethoxy, propoxy, butoxy or the like; or $C_2-C_6$ (preferably $C_2-C_4$) dialkylamino such as dimethylamino, diethylamino or the like; $R^3$ is hydrogen; $-(CH_2)_nCOOH$ where n is an integer of 1 to 5 (preferably 1 to 3); or

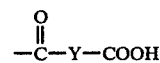

where Y is $-(CH_2)_m-$ (m is an integer of 1 to 3),

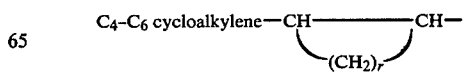

where r is an integer of 2 to 4, or

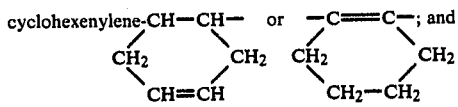

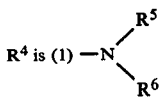

wherein $R^5$ and $R^6$ are independently $C_1$-$C_8$ (preferably $C_1$-$C_5$) alkyl such as methyl, ethyl, propyl, iso-propyl, butyl, iso-butyl, pentyl, hexyl, heptyl, octyl or the like or (2)

wherein A is a divalent radical which consists of two or more groups selected from methylene —$CH_2$— and monosubstituted

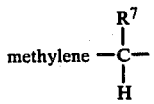

where $R^7$ is $C_1$-$C_5$ (preferably $C_1$-$C_3$) alkyl such as methyl, ethyl, propyl, butyl or the like or carbamoyl —$CONH_2$; and zero or one or more than one group selected from the group consisting of $$\text{imino} \quad -\overset{H}{\underset{|}{N}}-$$

and substituted $$\text{imino} \quad -\overset{R^8}{\underset{|}{N}}-$$

where $R^8$ is $C_1$-$C_5$ (preferably $C_1$-$C_3$) alkyl such as methyl, ethyl, propyl, butyl or the like, which are combined in an arbitory order to form a ring, the number of the combined groups being up to 9 (preferably 7).

Illustrative of the typical

groups are the following: 1-pyrrolidinyl, piperidino, 1-hexamethyleneiminyl, 1-heptamethyleneiminyl, 3-methyl-1-pyrrolidinyl, 2,5-dimethyl-1-pyrrolidinyl, 2-ethylpyrrolidinyl, 2-methylpiperidino, 3-methyl-piperidino, 4-methylpiperidino, 4-ethylpiperidino, 2,4-dimethylpiperidino, 4-methyl-1-piperazinyl, 4-ethyl-1-piperazinyl, 4-propyl-1-piperazinyl, 3-carbamoyl-1-pyrrolidinyl, 3-carbamoylpiperidino, 4-carbamoyl-piperidino.

The preferred

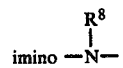

groups are 1-pyrrolidinyl, piperidino and $C_5$-$C_7$ 4-alkyl-1-piperazinyl, each of which is unsubstituted or substituted with one or two groups selected from $C_1$-$C_3$ alkyl and carbamoyl.

In the above formula (I), the 3-aminopropoxy group may be located at any of the 2- to 4-position of the benzene nucleus; preferably, it is located at either the 2- or 4-position, and more preferably it is located at the 2-position.

In the above formula (I), the substituent positions of $R^1$ and $R^2$ on the benzene nucleuses are not limited, preferably any of the 2'- to 4'-position and any of the 4- to 6-position, respectively.

Representative of the compounds of this invention are the following:
2-[(3-dimethylamino-2-hydroxy)propoxy]bibenzyl;
2-[(3-dimethylamino-2-carboxymethoxy)propoxy]bibenzyl;
2-[[3-dimethylamino-2-(2-carboxyethoxy)]propoxy]bibenzyl;
2-[[3-dimethylamino-2-(3-carboxypropoxy)]propoxy]bibenzyl;
2-[[3-dimethylamino-2-(3-carboxypropionyloxy)]propoxy]bibenzyl;
2-[[3-dimethylamino-2-(4-carboxybutyryloxy)]propoxy]bibenzyl;
2-[[3-dimethylamino-2-(2-carboxycyclobutylcarbonyloxy)]propoxy]bibenzyl;
2-[[3-dimethylamino-2-(2-carboxycyclopentylcarbonyloxy)]propoxy]bibenzyl;
2-[[3-dimethylamino-2-(2-carboxycyclohexylcarbonyloxy)]propoxy]bibenzyl;
2-[[3-dimethylamino-2-(2-carboxy-4-cyclohexenylcarbonyloxy)]propoxy]bibenzyl;
2-[[3-dimethylamino-2-(2-carboxy-1-cyclohexenylcarbonyloxy)]propoxy]bibenzyl;
2-[(3-diethylamino-2-hydroxy)propoxy]bibenzyl;
2-[(3-diethylamino-2-carboxymethoxy)propoxy]bibenzyl;
2-[[3-diethylamino-2-(2-carboxyethoxy)]propoxy]bibenzyl;
2-[[3-diethylamino-2-(3-carboxypropoxy)]propoxy]bibenzyl;
2-[[3-diethylamino-2-(3-carboxypropionyloxy)]propoxy]bibenzyl;
2-[[3-diethylamino-2-(4-carboxybutyryloxy)]propoxy]bibenzyl;
2-[[3-diethylamino-2-(2-carboxycyclobutylcarbonyloxy)]propoxy]bibenzyl;
2-[[3-diethylamino-2-(2-carboxycyclopentylcarbonyloxy)]propoxy]bibenzyl;
2-[[3-diethylamino-2-(2-carboxyhexylcarbonyloxy)]propoxy]bibenzyl;
2-[[3-diethylamino-2-(2-carboxy-4-cyclohexenylcarbonyloxy)]propoxy]bibenzyl;
2-[[3-diethylamino-2-(2-carboxy-1-cyclohexenylcarbonyloxy)]propoxy]bibenzyl;
2-[[3-(1-pyrrolidinyl)-2-hydroxy]propoxy]bibenzyl;
2-[[3-(1-pyrrolidinyl)-2-carboxymethoxy]propoxy]bibenzyl;
2-[[3-(1-pyrrolidinyl)-2-(2-carboxyethoxy)]propoxy]bibenzyl;
2-[[3-(1-pyrrolidinyl)-2-(3-carboxypropoxy)]propoxy]bibenzyl;
2-[[3-(1-pyrrolidinyl)-2-(3-carboxypropionyloxy)]propoxy]bibenzyl;
2-[[3-(1-pyrrolidinyl)-2-(4-carboxybutyryloxy)]propoxy]bibenzyl;
2-[[3-(1-pyrrolidinyl)-2-(2-carboxycyclobutylcarbonyloxy)]propoxy]bibenzyl;

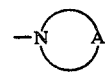

2-[[3-(1-pyrrolidinyl)-2-(2-carboxycyclopentylcarbonyloxy)]propoxy]bibenzyl;
2-[[3-(1-pyrrolidinyl)-2-(2-carboxycyclohexylcarbonyloxy)]propoxy]bibenzyl;
2-[[3-(1-pyrrolidinyl)-2-(2-carboxy-4-cyclohexenylcarbonyloxy)]propoxy]bibenzyl;
2-[[3-(1-pyrrolidinyl)-2-(2-carboxy-1-cyclohexenylcarbonyloxy)]propoxy]bibenzyl.
2-[(3-piperidino-2-hydroxy)propoxy]bibenzyl;
2-[(3-piperidino-2-carboxymethoxy)propoxy]bibenzyl;
2-[[3-piperidino-2-(2-carboxyethoxy)]propoxy]bibenzyl;
2-[[3-piperidino-2-(3-carboxypropoxy)]propoxy]bibenzyl;
2-[[3-piperidino-2-(3-carboxypropionyloxy)]propoxy]bibenzyl;
2-[[3-piperidino-2-(4-carboxybutyryloxy)]propoxy]bibenzyl;
2-[[3-piperidino-2-(2-carboxycyclobutylcarbonyloxy)]propoxy]bibenzyl;
2-[[3-piperidino-2-(2-carboxycyclopentylcarbonyloxy)]propoxy]bibenzyl;
2-[[3-piperidino-2-(2-carboxycyclohexylcarbonyloxy)]propoxy]bibenzyl;
2-[[3-piperidino-2-(2-carboxy-4-cyclohexenylcarbonyloxy)]propoxy]bibenzyl;
2-[[3-piperidino-2-(2-carboxy-1-cyclohexenylcarbonyloxy)]propoxy]bibenzyl.
2-[[3-(4-methylpiperidino)-2-hydroxy]propoxy]bibenzyl;
2-[[3-(4-methylpiperidino)-2-carboxymethoxy]propoxy]bibenzyl;
2-[[3-(4-methylpiperidino)-2-(2-carboxyethoxy)]propoxy]bibenzyl;
2-[[3-(4-methylpiperidino)-2-(3-carboxypropoxy)]propoxy]bibenzyl;
2-[[3-(4-methylpiperidino)-2-(3-carboxypropionyloxy)]propoxy]bibenzyl;
2-[[3-(4-methylpiperidino)-2-(4-carboxybutyryloxy)]propoxy]bibenzyl;
2-[[3-(4-methylpiperidino)-2-(2-carboxycyclobutylcarbonyloxy)]propoxy]bibenzyl;
2-[[3-(4-methylpiperidino)-2-(2-carboxycyclopentylcarbonyloxy)]propoxy]bibenzyl;
2-[[3-(4-methylpiperidino)-2-(2-carboxycyclohexylcarbonyloxy)]propoxy]bibenzyl;
2-[[3-(4-methylpiperidino)-2-(2-carboxy-4-cyclohexenylcarbonyloxy)]propoxy]bibenzyl;
2-[[3-(4-methylpiperidino)-2-(2-carboxy-1-cyclohexenylcarbonyloxy)]propoxy]bibenzyl.
2-[[3-(4-methyl-1-piperazinyl)-2-hydroxy]propoxy]bibenzyl;
2-[[3-(4-methyl-1-piperazinyl)-2-carboxymethoxy]propoxy]bibenzyl;
2-[[3-(4-methyl-1-piperazinyl)-2-(2-carboxyethoxy)]propoxy]bibenzyl;
2-[[3-(4-methyl-1-piperazinyl)-2-(3-carboxypropoxy)]propoxy]bibenzyl;
2-[[3-(4-methyl-1-piperazinyl)-2-(3-carboxypropionyloxy)]propoxy]bibenzyl;
2-[[3-(4-methyl-1-piperazinyl)-2-(4-carboxybutyryloxy)]propoxy]bibenzyl;
2-[[3-(4-methyl-1-piperazinyl)-2-(2-carboxycyclobutylcarbonyloxy)]propoxy]bibenzyl;
2-[[3-(4-methyl-1-piperazinyl)-2-(2-carboxycyclohexylcarbonyloxy)]propoxy]bibenzyl;
2-[[3-(4-methyl-1-piperazinyl)-2-(2-carboxy-4-cyclohexenylcarbonyloxy)]propoxy]bibenzyl;
2-[[3-(4-methyl-1-piperazinyl)-2-(2-carboxy-1-cyclohexenylcarbonyloxy)]propoxy]bibenzyl;
2-[[3-(4-carbamoylpiperidino)-2-hydroxy]propoxy]bibenzyl;
2-[[3-(4-carbamoylpiperidino)-2-carboxymethoxy]propoxy]bibenzyl;
2-[[3-(4-carbamoylpiperidino)-2-(2-carboxyethoxy)]propoxy]bibenzyl;
2-[[3-(4-carbamoylpiperidino)-2-(3-carboxypropoxy)]propoxy]bibenzyl;
2-[[3-(4-carbamoylpiperidino)-2-(3-carboxypropionyloxy)]propoxy]bibenzyl;
2-[[3-(4-carbamoylpiperidino)-2-(4-carboxybutyryloxy)]propoxy]bibenzyl;
2-[[3-(4-carbamoylpiperidino)-2-(2-carboxycyclobutylcarbonyloxy)]propoxy]bibenzyl;
2-[[3-(4-carbamoylpiperidino)-2-(2-carboxycyclopentylcarbonyloxy)]propoxy]bibenzyl;
2-[[3-(4-carbamoylpiperidino)-2-(2-carboxycyclohexylcarbonyloxy)]propoxy]bibenzyl;
2-[[3-(4-carbamoylpiperidino)-2-(2-carboxy-4-cyclohexenylcarbonyloxy)]propoxy]bibenzyl;
2-[[3-(4-carbamoylpiperidino)-2-(2-carboxy-1-cyclohexenylcarbonyloxy)]propoxy]bibenzyl.

The above examples are exemplary of those compounds of Formula (I) wherein $R^1$ and $R^2$ are hydrogen and $R^4$ is dimethylamino, diethylamino, 1-pyrrolidinyl, piperidino, 4-methylpiperidino, 4-methyl-1-piperazinyl or 4-carbamoylpiperidino.

Similarly, these respective corresponding compounds in which $R^2$ is hydrogen and $R^1$ is fluoro, chloro, methoxy, methyl or dimethylamino or $R^1$ is hydrogen and $R^2$ is fluoro, chloro or methoxy are also illustrative of the compounds of this invention.

The pharmaceutically acceptable acid addition salts of the above compounds are, of course, also included within the scope of this invention.

It will be understood that the term "pharmaceutically acceptable acid addition salts" as used herein is intended to include non-toxic salts of the compounds of this invention with an anion.

Representative of such salts are hydrochlorides, hydrobromides, sulfates, phosphates, nitrates, acetates, succinates, adipates, propionates, tartrates, maleates, oxalates, citrates, benzoates, toluenesulfonates and methanesulfonates.

Of the compounds of this invention, it will be understood that the following compounds are most preferred due to their high level of ability to inhibit the platelet aggregation.

2-[(3-dimethylamino-2-hydroxy)propoxy]bibenzyl hydrochloride
2-[(3-dimethylamino-2-hydroxy)propoxy]-3'-methoxybibenzyl hydrochloride
2-[[3-dimethylamino-2-(3-carboxypropionyloxy)]propoxy]bibenzyl hydrochloride
2-[[3-dimethylamino-2-(3-carboxypropionyloxy)]propoxy]-3'-methoxybibenzyl hydrochloride
2-[(3-dimethylamino-2-carboxymethoxy)propoxy]bibenzyl hydrochloride
2-[[3-dimethylamino-2-(2-carboxyethoxy)]propoxy]bibenzyl hydrochloride
2-[[3-dimethylamino-2-(2-carboxyethoxy)]propoxy]-3'-methoxybibenzyl hydrochloride.

The above compounds are intended only to illustrate the typical compounds of this invention, and the above listing is not to be construed as limiting the scope of the invention.

The method for preparing the compounds according to this invention will be described below.

The compound of the formula (I) wherein $R^3$ is hydrogen, that is, (3-aminopropoxy)bibenzyl derivative of the formula (V);

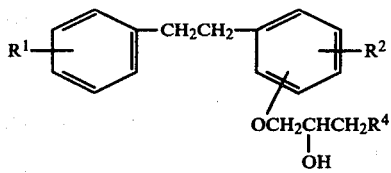

wherein $R^1$, $R^2$ and $R^4$ are as defined in Formula (I), can be prepared by reacting an epoxy derivatives of the formula (III):

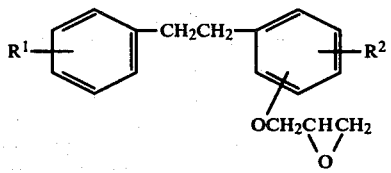

wherein $R^1$ and $R^2$ are as defined in Formula (I), with an amine of the formula (IV);

$$R^4H \quad (IV)$$

wherein $R^4$ is as defined in Formula (I) in a suitable solvent such as water, alcohol, tetrahydrofuran, acetone and the like at a temperature of from room temperature to the boiling point of the solvent. The epoxy derivatives of the formula (III) above can be prepared by reacting a hydroxybibenzyl of the formula (II):

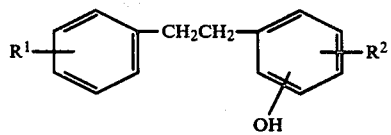

wherein $R^1$ and $R^2$ are as defined in Formula (I), with epichlorhydrin in an aprotic solvent such as dimethyl formamide, tetrahydrofuran and benzene in the presence of a metal hydride such as sodium hydride or in a alcohol such as methanol and ethanol in the presence of a metal alcoholate.

The reaction temperature may vary from room temperature to the boiling point of the solvent.

The compound of the formula (I) wherein $R^3$ is

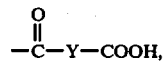

that is, (3-aminopropoxy)bibenzyl derivative of the formula (VII):

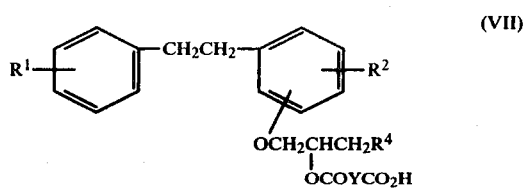

wherein $R^1$, $R^2$, $R^4$ and Y are as defined in Formula (I), can be prepared by reacting the (3-aminopropoxy)bibenzyl derivative of the formula (V) with an acid anhydride of the formula (VI):

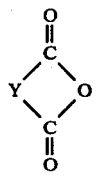

wherein Y is as defined in Formula (I), the reaction can be carried out by heating the mixture in an aprotic solvent such as tetrahydrofuran.

The compound of the formula (I) wherein $R^3$ is $-(CH_2)_n-COOH$, that is (3-aminopropoxy)bibenzyl derivative of the formula (X):

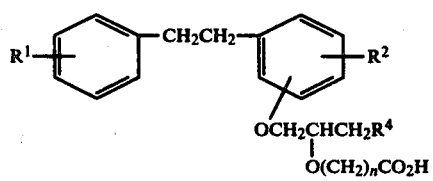

wherein $R^1$, $R^2$, $R^4$ and n are as defined in Formula (I), can be prepared by the alkaline hydrolysis of a (3-aminopropoxy)bibenzyl derivative of the formula (IX):

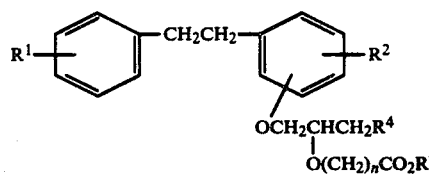

wherein $R^1$, $R^2$, $R^4$ and n are as defined in Formula (I) and $R^9$ is lower alkyl.

The (3-aminopropoxy)bibenzyl derivatives (IX) above can be prepared either by reacting the (3-aminopropoxy)bibenzyl derivative (V) with an ω-halogenoalkanoic acid ester of the formula (VIII):

$$X(CH_2)_nCO_2R^9 \quad (VIII)$$

wherein n is as defined in Formula (I), X is halogen and $R^9$ is lower alkyl, in a tertiary alcohol in the presence of a metal salt of the tertiary alcohol, or by reacting the compound (V) with methyl acrylate without solvents or in an aprotic solvent such as dimethylformamide in the presence of a metal hydride.

Pharmacological testing of the (3-aminopropoxy)bibenzyl derivatives of this invention has demonstrated that they possess anticoagulant activity, especially activity against blood platelet aggregation, and are suitable for use in the cure and prevention of thrombosis. Their activity against blood platelet aggregation can be demonstrated by an increase or decrease in platelet aggregation value caused by the administration of the compounds of this invention to rabbits.

Evaluation of the compounds of this invention for their activity against platelet aggregation was carried out according to a turbidometric method described by G. V. R. Born, Nature, 194, 927 (1962). Platelet aggregation was measured using platelet-rich plasma prepared from citrated blood which was collected from a carotid artery of male white rabbits of Japanese native kind. A suspension of collagen (bovine Achilles tendon collagen, Sigma) in saline was used to cause platelet aggregation. The aggregation of rabbit blood platelet was induced by adding the suspension of collagen to give 10 to 15 $\mu$g collagen per milliliter. At this time, the tests were conducted at 37° C. at levels of $4 \times 10^5$ platelet/mm$^3$. A solution of compounds of this invention in saline was added to the platelet-rich plasma. After three minutes of preincubation with the platelet-rich plasma, collagen was added to cause platelet aggregation. Percent inhibition was calculated by comparison with controls.

The concentration of the compound in micromoles inhibiting platelet aggregation by 50 percent ($I_{50}$) are shown in Table 1.

$LD_{50}$ was determined by Litchfield-Wilcoxon method. The $LD_{50}$ values of the compounds of this invention are in the range of 2,000 to 5,000 mg/kg (in mice p.o.), for example, the $LD_{50}$ of 2-[[3-dimethylamino-2-(3-carboxyethoxy)]propoxy]bibenzyl is above 3,000 mg/kg (p.o.).

The compounds of this invention can be administered by any means that effects inhibiting blood platelet aggregation in warm-blooded animals.

For example, administration can be parenterally, subcutaneously, intravenously, intramuscularly, or intraperitoneally. Alternatively or concurrently, administration can be by the oral route. The dosage administered will be dependent upon the age, health and weight of the recipient, kind of concurrent treatment if any, frequency of treatment, and the nature of the effect desired. Generally, a daily dosage of active ingredient compound will be from about 0.5 to 50 mg per kg of body weight. Normally, from 1 to 30 mg per kg per day, in one or more applications per day is effective to obtain the desired result.

The compound of this invention can be employed in dosage forms such as tablets, capsules, powder packets, or liquid solutions, or elixirs, for oral administration, or sterile liquid formulations such as solutions or suspensions for parenteral use. In such compositions, besides the active ingredient of this invention, the composition will contain a solid or liquid non-toxic pharmaceutical carrier for the active ingredient. In one embodiment of a composition, the solid carrier can be a capsule of the ordinary gelatin type. In another embodiment, the active ingredient can be tableted with or without adjuvants, or put into powder packets. These capsules, tablets and powders will generally constitute from about 5% to about 95% and preferably from 25% to 90% by weight of active ingredient. These dosage forms preferably contain from about 5 to about 500 mg of active ingredient, with from about 25 to about 250 mg being most preferred.

The pharmaceutical carrier can be a sterile liquid such as water and oils, including those of petroleum, animal, vegetable or synthetic origin, such as peanut oil, soybean oil, mineral oil, sesame oil, and the like.

In general, water saline, aqueous dextrose and related sugar solutions, and glycols such as propylene glycol and polyethylene glycol are preferred liquid carriers, particularly for injectible solutions such as saline will ordinarily contain from about 0.5% to 20% and preferably about 1 to 10% by weight of the active ingredient.

As mentioned above, oral administration can be in a suitable suspension or syrup, in which the active ingredient normally will constitute from about 0.5 to 10% by weight. The pharmaceutical carrier in such composition can be a watery vehicle such as an aromatic water, a syrup or a pharmaceutical mucilage.

Having generally described the invention, a more complete understanding can be obtained by reference to certain specific examples, which are included for purposes of illustration only and are not intended to be limiting unless otherwise specified.

EXAMPLE 1

2-[(3-dimethylamino-2-hydroxy)propoxy]bibenzyl hydrochloride

To a suspension of 2.2 g of 60% sodium hydride in 30 ml of N,N-dimethylformamide was added dropwise a solution of 10 g of 2-hydroxybenzyl in 30 ml of N,N-dimethylformamide under stirring and ice-cooling. After completion of the dropwise addition, 23.4 g of epichlorhydrin was added in one portion. The ice bath was removed and the mixture was stirred for 3 to 4 hours at room temperature. The reaction solvent was then distilled off in vacuo and 40 ml of benzene and 20 ml of water were added to the residue. After the aqueous layer was separated, the benzene layer was washed with water and the benzene was distilled off in vacuo to give an oily epoxide.

To the epoxide obtained above were added 40 ml of tetrahydrofuran and 53 ml of aqueous 50% dimethylamine and the mixture was stirred for 4 to 5 hours at room temperature. After the tetrahydrofuran and dimethylamine were distilled off in vacuo, 50 ml of isopropyl ether and 10 ml of water were added and the aqueous layer was separated. The isopropyl ether layer was washed with water and dried over anhydrous sodium sulfate followed by addition of 9.7 ml of 20% hydrogen chloride in ethyl acetate under stirring and ice-cooling. The resulting crystals were collected by filtration and recrystallized from ethyl acetate to give 14.4 g (85% yield) of 2-[(3-dimethylamino-2-hydroxy)propoxy]bibenzyl hydrochloride.

The properties of this compound are shown in Table 1 as Compound 1.

Likewise, Compounds 2 and 3 were prepared in the same way and their properties are also shown in Table 1.

EXAMPLE 2

2-[[3-dimethylamino-2-(3-carboxypropionyloxy)]-propoxy]bibenzyl hydrochloride

To a solution of 5 g of 2-[(3-dimethylamino-2-hydroxy)propoxy]bibenzyl in 25 ml of tetrahydrofuran was added 1.9 g of succinic anhydride and the mixture was stirred for 3 hours under heating at reflux. After completion of the reaction, the reaction solvent was distilled off in vacuo and the residue was dissolved in 20 ml of chloroform.

To the solution was added 3.2 ml of 20% hydrogen chloride in ethyl acetate under stirring and ice-cooling followed by addition of 80 ml of ether. The resulting crystals were collected by filtration and recrystallized from acetone to give 6.6 g (91% yield) of 2-[[3-dimethylamino-2-(3-carboxypropionyloxy)]propoxy]bibenzyl hydrochloride. The properties of this compound are shown in Table 1 as Compound 4.

Likewise, Compounds 5 to 11, 15 and 16 were prepared in the same way and their properties are also shown in Table 1.

EXAMPLE 3

2-[(3-dimethylamino-2-carboxymethoxy)propoxy]bibenzyl hydrochloride

To a solution of 8.1 g of 2-[(3-dimethylamino-2-hydroxy)propoxy]bibenzyl in 60 ml of tert-butanol was added 6.2 g of potassium tert-butoxide and the mixture was stirred at 70° C. for 20 minutes. After cooling to room temperature, 4.9 g of tert-butyl chloroacetate was added dropwise under stirring. After completion of the dropwise addition, the reaction mixture was allowed to stand for 1 hour and then 1.6 g of tert-butyl chloroacetate was further added dropwise. After stirring for 2 hours, 40 ml of 2N sodium hydroxide solution was added and the mixture was stirred at 50° C. for 2 hours. After completion of the reaction, ether was added and the aqueous layer was removed to extract the unreaction mixture. The ether layer was extracted twice with 0.5N sodium hydroxide solution and then the extract was combined with the original aqueous layer. The solution was adjusted to pH 3 with hydrochloric acid and extracted with chloroform. The extract was dried over anhydrous sodium sulfate and the solvent was distilled off. The residue was dissolved in acetone and 20% hydrogen chloride in ethyl acetate was added under cooling. The resulting crystals were collected by filtration and recrystallized from acetone to give 6.6 g (62% yield) of 2-[(3-dimethylamino-2-carboxymethoxy)propoxy]bibenzyl hydrochloride.

The properties of this compound are shown in Table 1 as Compound 12.

EXAMPLE 4

2-[[3-dimethylamino-2-(2-carboxyethoxy)]propoxy]bibenzyl hydrochloride

To 10 g of 2-[(3-dimethylamino-2-hydroxy)propoxy]bibenzyl was added 0.1 g of 60% sodium hydride and the mixture was stirred for 15 minutes at room temperature. Thereafter, 14.4 g of methyl acrylate was added in one portion and the mixture was stirred for 3 hours at room temperature. After completion of the reaction, 100 ml of ether and 50 ml of water were added and the aqueous layer was removed. The ether layer was washed with water and subjected to vacuum distillation. The resulting residue was dissolved in 30 ml of methanol and 33 ml of 2N sodium hydroxide solution was added. The mixture was stirred for 3 hours at room temperature. After completion of the reaction, ether was added and the aqueous layer was removed to extract the unreaction mixture. The ether layer was extracted twice with 0.5N sodium hydroxide solution and then the extract was combined with the original aqueous layer. The solution was adjusted to pH 3 with hydrochloric acid and extracted with chloroform. The extract was dried over anhydrous sodium sulfate and the solvent was distilled off. The residue was dissolved in acetone and 20% hydrogen chloride in ethyl acetate was added under stirring and ice-cooling. The resulting crystals were collected by filtration and recrystallized from acetone to give 9.8 g (72% yield) of 2-[[3-dimethylamino-2-(2-carboxyethoxy)]propoxy]bibenzyl hydrochloride.

The properties of this compound are shown in Table 1 as Compound 13.

Likewise, Compounds 14 and 17 were prepared in the same way and their properties are also shown in Table 1.

TABLE 1

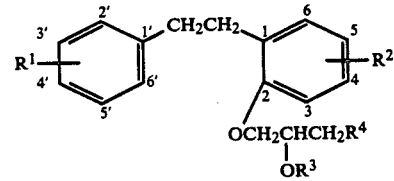

| No. | $R^1$ | $R^2$ | $R^3$ | $R^4$ | Addition salt |
|---|---|---|---|---|---|
| 1 | H | H | H | $-N(CH_3)_2$ | HCl |
| 2 | 4'-$N(CH_3)_2$ | H | H | $-N(CH_3)_2$ | 2HCl |
| 3 | 3'-$OCH_3$ | H | H | $-N(CH_3)_2$ | HCl |
| 4 | H | H | $-CO(CH_2)_2CO_2H$ | $-N(CH_3)_2$ | HCl |
| 5 | 4'-$N(CH_3)_2$ | H | $-CO(CH_2)_2CO_2H$ | $-N(CH_3)_2$ | 2HCl |
| 6 | 3'-$OCH_3$ | H | $-CO(CH_2)_2CO_2H$ | $-N(CH_3)_2$ | HCl |
| 7 | 3'-F | H | $-CO(CH_2)_2CO_2H$ | $-N(CH_3)_2$ | HCl |
| 8 | 3'-Cl | H | $-CO(CH_2)_2CO_2H$ | $-N(CH_3)_2$ | HCl |
| 9 | H | 5-Cl | $-CO(CH_2)_2CO_2H$ | $-N(CH_3)_2$ | HCl |
| 10 | H | H | 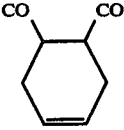 | $-N(CH_3)_2$ | HCl |

TABLE 1-continued

| No. | | | | | |
|---|---|---|---|---|---|
| 11 | H | H | —CO—◇—CO₂H (cyclobutane) | —N(CH₃)₂ | HCl |
| 12 | H | H | —CH₂CO₂H | —N(CH₃)₂ | HCl |
| 13 | H | H | —(CH₂)₂CO₂H | —N(CH₃)₂ | HCl |
| 14 | 3'-OCH₃ | H | —(CH₂)₂CO₂H | —N(CH₃)₂ | HCl |
| 15 | H | H | —CO(CH₂)₂CO₂H | —N(piperidinyl) | HCl |
| 16 | H | H | —CO(CH₂)₂CO₂H | —N(4-carbamoylpiperidinyl) | HCl |
| 17 | 2'-CH₃ | H | —(CH₂)₂CO₂H | —N(C₂H₅)₂ | HCl |

| No. | m.p. (°C.) | Molecular formula | Elementary analysis Upper: Calcd. (%) Lower: Found (%) | | | I₅₀ (μM) |
|---|---|---|---|---|---|---|
| | | | C | H | N | |
| 1 | 101–3 | C$_{19}$H$_{25}$NO$_2$·HCl | 67.94 | 7.80 | 4.17 | 1.5 |
| | | | 68.38 | 7.72 | 3.97 | |
| 2 | 146–8 | C$_{21}$H$_{30}$N$_2$O$_2$·2HCl | 60.72 | 7.76 | 6.74 | 0.75 |
| | | | 60.60 | 7.65 | 6.80 | |
| 3 | 120–1 | C$_{20}$H$_{27}$NO$_3$·HCl | 65.65 | 7.71 | 3.83 | 0.8 |
| | | | 65.55 | 7.65 | 3.80 | |
| 4 | 146–9 | C$_{23}$H$_{29}$NO$_5$·HCl | 63.37 | 6.94 | 3.21 | 2 |
| | | | 63.39 | 6.87 | 3.07 | |
| 5 | powder | C$_{25}$H$_{34}$N$_2$O$_5$·2HCl | 58.25 | 7.04 | 5.43 | 1.5 |
| | | | 58.05 | 7.00 | 5.60 | |
| 6 | 139–42 | C$_{24}$H$_{31}$NO$_6$·HCl | 61.86 | 6.92 | 3.01 | 1.5 |
| | | | 61.84 | 6.89 | 2.98 | |
| 7 | 142–4 | C$_{23}$H$_{28}$FNO$_5$·HCl | 60.86 | 6.44 | 3.09 | 1.2 |
| | | | 60.80 | 6.39 | 2.96 | |
| 8 | 158–61 | C$_{23}$H$_{28}$ClNO$_5$·HCl | 58.73 | 6.21 | 2.98 | 0.8 |
| | | | 58.53 | 6.15 | 2.86 | |
| 9 | 160–1 | C$_{23}$H$_{28}$ClNO$_5$·HCl | 58.73 | 6.21 | 2.98 | 4 |
| | | | 58.58 | 6.19 | 2.96 | |
| 10 | 160–3 | C$_{27}$H$_{33}$NO$_5$·HCl | 66.45 | 7.02 | 2.87 | 8.0 |
| | | | 66.28 | 6.97 | 2.92 | |
| 11 | 107–10 | C$_{25}$H$_{32}$NO$_5$·HCl | 64.85 | 7.18 | 3.03 | 5.5 |
| | | | 64.80 | 7.13 | 3.29 | |
| 12 | 107–10 | C$_{21}$H$_{27}$NO$_4$·HCl | 64.03 | 7.16 | 3.56 | 4.5 |
| | | | 64.00 | 7.05 | 3.49 | |
| 13 | 109–10 | C$_{22}$H$_{29}$NO$_4$·HCl | 64.78 | 7.41 | 3.43 | 3.0 |
| | | | 64.60 | 7.31 | 3.40 | |
| 14 | 140–2 | C$_{23}$H$_{31}$NO$_5$·HCl | 63.08 | 7.36 | 3.20 | 3.0 |
| | | | 62.90 | 7.25 | 3.30 | |
| 15 | 158–61 | C$_{26}$H$_{33}$NO$_5$·HCl | 65.60 | 7.20 | 2.94 | 2.5 |
| | | | 65.51 | 7.10 | 2.83 | |
| 16 | 86–90 | C$_{27}$H$_{34}$N$_2$O$_6$·HCl | 62.48 | 6.80 | 5.40 | 3 |
| | | | 62.29 | 6.63 | 5.52 | |
| 17 | 176–8 | C$_{25}$H$_{35}$NO$_4$·HCl | 66.72 | 8.06 | 3.11 | — |
| | | | 66.42 | 7.99 | 3.13 | |

The following compounds can be prepared in the same manner as disclosed in the above examples:

2-[[3-(1-pyrrolidinyl)-2-(2-carboxyethoxy)]propoxy]-3'-methoxybibenzyl hydrochloride 2-[[3-(4-methyl-1-piperazinyl)-2-(3-carboxypropionyloxy)]propoxy]bibenzyl hydrochloride 2-[[3-(4-methylpiperidino)-2-carboxymethoxy)]propoxy]-3'-fluorobibenzyl hydrochloride 2-[[3-dimethylamino-2-(2-carboxy-1-cyclohexenylcarbonyloxy)]propoxy]bibenzyl hydrochloride 2-[[3-dimethylamino-2-(3-carboxypropionyloxy)]propoxy]-3'-methoxy-5-chlorobibenzyl hydrochloride

Having now fully described the invention, it will be apparent to one of ordinary skill in the art that many changes and modifications can be made thereto without departing from the spirit of the invention as set forth herein.

What claimed as new and intended to be covered by Letters Patent is:

1. A (3-aminopropoxy)bibenzyl derivative of the formula (I):

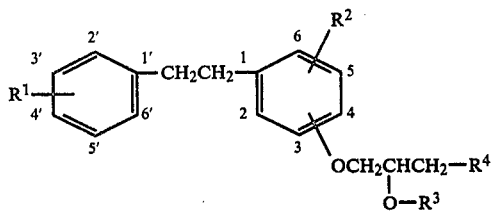 (I)

wherein $R^1$ and $R^2$ independently are hydrogen, halogen, $C_1$-$C_5$ alkyl, $C_1$-$C_5$ alkoxy or $C_2$-$C_6$ dialkylamino; $R^3$ is hydrogen, —$(CH_2)_n$—COOH where n is an integer of 1 to 5, or

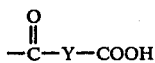

where Y is —$(CH_2)_m$— (m is an integer of 1 to 3),

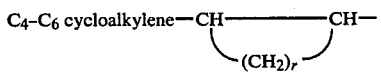

where r is an integer of 2 to 4, or

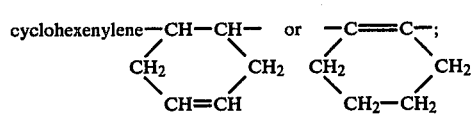

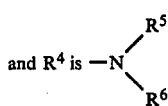

wherein $R^5$ and $R^6$ independently are $C_1$-$C_8$ alkyl or a pharmaceutically acceptable acid addition salt thereof.

2. The compound of claim 1 wherein $R^1$ and $R^2$ independently are hydrogen, halogen, $C_1$-$C_3$ alkyl, $C_1$-$C_3$ alkoxy or $C_2$-$C_4$ dialkylamino; $R^3$ is hydrogen, —$(CH_2)_n$—COOH where n is an integer of 1 to 3, or

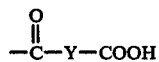

where Y is —$(CH_2)_m$— (m is an integer of 1 to 3),

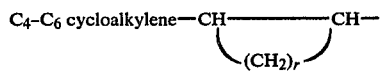

where r is an integer of 2 to 4, or

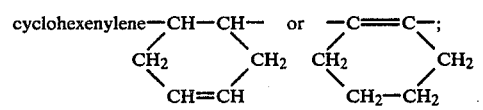

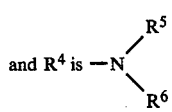

wherein $R^5$ and $R^6$ independently are $C_1$-$C_5$ alkyl.

3. The compound of claim 2 wherein $R^1$ and $R^2$ independently are hydrogen, fluorine, chlorine, $C_1$-$C_3$ alkyl, $C_1$-$C_3$ alkoxy or $C_2$-$C_4$ dialkylamino; $R^3$ is hydrogen, —$(CH_2)_n$—COOH where n is an integer of 1 to 3, or

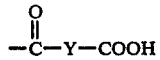

where Y is —$(CH_2)_m$— (m is an integer of 1 to 3),

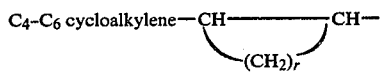

where r is an integer of 2 to 4, or

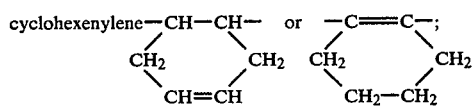

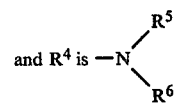

wherein $R^5$ and $R^6$ indepedently are $C_1$-$C_5$ alkyl and $R^1$, $R^2$ and

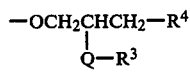

are respectively located at any of the 2'- to 4'-position, any of the 4- to 6-position and the 2-position.

4. The compound of claim 3 which is 2-[(3-dimethylamino-2-hydroxy)propoxy]bibenzyl hydrochloride.

5. The compound of claim 3 which is 2-[(3-dimethylamino-2-hydroxy)propoxy]-3'-methoxybibenzyl hydrochloride.

6. The compound of claim 3 which is 2-[[3-dimethylamino-2-(3-carboxypropionyloxy)]propoxy]bibenzyl hydrochloride.

7. The compound of claim 3 which is 2-[[3-dimethylamino-2-(3-carboxypropionyloxy)]propoxy]-3'-methoxybibenzyl hydrochloride.

8. The compound of claim 3 which is 2-[(3-dimethylamino-2-carboxymethoxy)propoxy]bibenzyl hydrochloride.

9. The compound of claim 3 which is 2-[[3-dimethylamino-2-(2-carboxyethoxy)]propoxy]bibenzyl hydrochloride.

10. The compound of claim 3 which is 2-[[3-dimethylamino-2-(2-carboxyethoxy)]propoxy]-3'-methoxybibenzyl hydrochloride.

11. A pharmaceutical composition which comprises an amount of a compound of claim 1 effective for inhibiting platelet aggregation and a pharmaceutically acceptable carrier.

12. A method of inhibiting platelet aggregation in blood of warm blooded animals which comprises administering to said animal an effective amount of a compound of claim 1.

13. A process for producing a compound of claim 1 which comprises (i) reacting a hydroxybibenzyl of the formula (II):

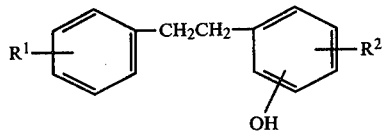

(II)

wherein R¹ and R² are as defined in Formula (I), with epichlorhydrin to give an epoxide of the formula (III):

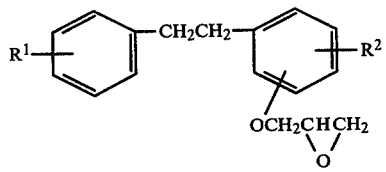

(III)

wherein R¹ and R² are as defined in Formula (I), (ii) reacting the epoxide (III) above with an amine of the formula (IV):

R⁴H  (IV)

wherein R⁴ is as defined in Formula (I) to form a (3-aminopropoxy)bibenzyl derivative of the formula (V):

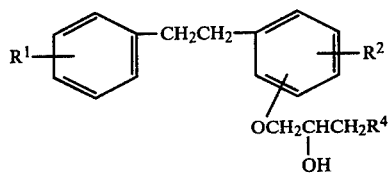

(V)

wherein R¹, R² and R⁴ are as defined in Formula (I), and if necessary, (iii) reacting the above compound of formula (V) with methyl acrylate in the presence of a metal halide or an ω-halogenoalkanoic acid ester of the formula (VIII):

$$X(CH_2)_nCO_2R^9$$  (VIII)

wherein n is as defined in Formula (I), X is halogen and R⁹ is lower alkyl, followed by hydrolysis, or with an acid anhydride of the formula (VI):

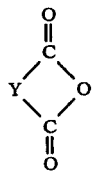

(VI)

wherein Y is as defined in Formula (I).

* * * * *